Figure 1:
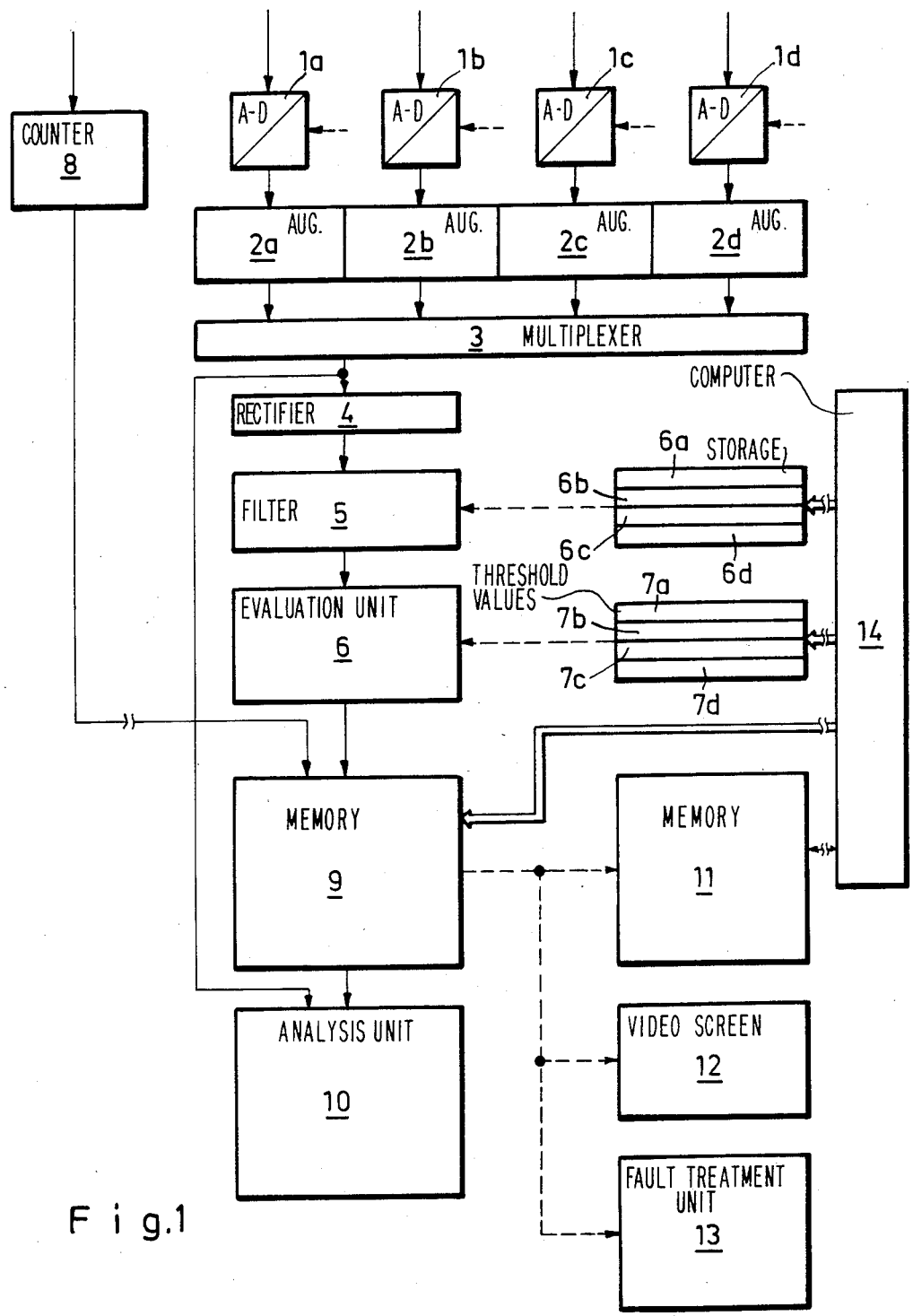

United States Patent [19]

Böttger et al.

[11] Patent Number: 4,646,572
[45] Date of Patent: Mar. 3, 1987

[54] METHOD FOR NON-DESTRUCTIVE TESTING WITH GUIDED WAVES

[75] Inventors: Wolfgang Böttger; Heinz Schneider, both of Dusseldorf; Willi Weingarten, Krefeld, all of Fed. Rep. of Germany

[73] Assignee: Mannesmann Aktiengesellschaft, Fed. Rep. of Germany

[21] Appl. No.: 641,264

[22] Filed: Aug. 16, 1984

[30] Foreign Application Priority Data

Aug. 29, 1983 [DE] Fed. Rep. of Germany ....... 3331468

[51] Int. Cl.$^4$ .......................................... G01N 29/04
[52] U.S. Cl. ........................................ 73/602; 73/620
[58] Field of Search ............... 73/602, 609, 620, 622, 73/626, 628, 598, 618, 637, 638; 364/507

[56] References Cited

U.S. PATENT DOCUMENTS

| | | | |
|---|---|---|---|
| 3,512,400 | 5/1970 | Lynnworth | 73/598 |
| 3,868,847 | 3/1975 | Gunkel | 73/622 |
| 3,955,405 | 5/1976 | Couture | 73/609 |
| 3,999,422 | 12/1976 | Lehmann et al. | 73/626 |
| 4,041,774 | 8/1977 | Morris et al. | 73/629 |
| 4,092,868 | 6/1978 | Thompson et al. | 73/638 |
| 4,229,796 | 10/1980 | Garrett | 73/622 |
| 4,271,705 | 6/1981 | Crostack | 73/602 |
| 4,408,228 | 10/1983 | Mahoney | 73/620 |

OTHER PUBLICATIONS

J. Szilard, *Ultrasonic Testing*, Wiley, N.Y., 1982, p. 606.
Couchman et al., "Computerized Signal Processing for Detecting Cracks Under Installed Fasteners", *Ultrasonics*, vol. 14, No. 6 (Nov. 1976), pp. 256–262.

*Primary Examiner*—Stephen A. Kreitman
*Assistant Examiner*—John E. Chapman, Jr.
*Attorney, Agent, or Firm*—Oldham, Oldham & Weber Co.

[57] ABSTRACT

The invention relates to a method for the interference-free testing with guided waves for faults, through cyclic production and reception of ultrasonic waves, through assessment of the received HF-signals for signal components, which derive from faults and through evaluation of the result. In order to reliably improve the capabiliy of assessing the received HF-signal over the greatest possible lengths covered and thereby to enable the testing for faults to be carried out at a high speed and a high degree of reliability, it is proposed that the received HF-signals are digitalized within the cycle and that from the digital HF-signals of several successive cycles average values are formed and these are likewise rectified with the aid of a computer and in each case are filtered and assessed with a threshold value characteristic and if required a signal analysis for faults in the testing path.

1 Claim, 1 Drawing Figure

METHOD FOR NON-DESTRUCTIVE TESTING WITH GUIDED WAVES

The invention relates to a method for non-destructive testing of a test piece with guided waves for faults through cyclic production and reception of ultrasonic waves.

Conventional ultrasonic testing equipment operates with free ultrasound and therefore operates with short pulse lengths and short sound paths. Operations are usually carried out with shutters and fault anticipation zones, in which then a simple threshold evaluation of the rectified HF signal takes place. Such a method is described in the German document laid open to public inspection No. 26 32 680. A general disadvantage of all equipment operating with free ultrasonic waves lies in that the effective testing surface is very small and therefore the test piece must be covered in very tightly packed traces. This considerably reduces the testing speed or makes it necessary to use equipment with several channels. A further disadvantage of such methods is the poor detectability of faults lying obliquely.

In addition, the production of ultrasonic waves is generally known, which in literature are termed guided waves. In this case, the testing field is very large and a testing for faults can be carried out over several meters in one test cycle, which leads to high test speeds. The great lengths covered by the ultrasonic waves have the disadvantage, however, that the damping capacity and transit-time effects have an unfavourable influence on the received ultrasonic waves. For example, analog indications of the ultrasonic waves reflected from distant material faults only stand out a little from the noise level. These damping and transit-time effects increase the susceptibility of the equipment to interference and impair the reliability of the product testing.

The object of the invention is to improve the ability of the received HF-signal to be evaluated reliably over the greatest possible lengths covered and thereby to enable the testing for faults to be carried out at a high speed and a high degree of reliability.

The solution to the problem is a method for non-destructive testing of a test piece with guided waves for faults through cyclic production and reception of ultrasonic waves, through assessment of the received HF-signals for signal components, which derive from faults and through evaluation of the result, characterized in that the received HF-signals are digitalized within the cycle and that from the digital HF-signals of several successive cycles average values are formed and these are rectified with the aid of a computer and in each case are filtered and are assessed by an assessment unit with a threshold value characteristic and a signal analysis for faults in the testing path.

For a complete understanding of the objects, techniques, and structure of the invention, reference should be had to the following detailed description and accompanying drawing wherein FIG. 1 is a schematic illustration of a testing installation according to the invention.

The method according to the invention reduces the greater susceptibility to interference caused by damping and time-transit effects. The testing with guided waves requires narrow band receiving units. In analog operations, this causes a high degree of susceptibility to interference and requires great resources in adjustment to reduce it. These disadvantages are avoided through the evaluation of the digitalized HF-signal. In a further step a digital averaging of the HF-signal is carried out via a freely selectable number of testing cycles, in order to clear the received signal from interference statistically and to minimize noise levels and consequently receive the coherent signal component amplified. If required, the averaged HF signals are further improved through rectifying in the noise ratio and in each case cleared of interference through digital filtering in the time or frequency range. In this, the proposal takes advantage of the fact that digital filters, as against analog filters, can also realize ideal or acausal filter characteristics.

This filter stage is important particularly for the time-multiplex and/or multi-mode operation, because here owing to different stimulus and propagation mechanisms the fault reflection behaviour is different so that a filtering with the respectively optimum filter characteristics is necessary, before the signals are subjected to further evaluation criteria.

The next data processing stage is a threshold evaluation of the digitalized HF-signal over the entire testing length with a threshold characteristic, which also takes into account the reduction in amplitude for the damping, subject to transit time, of the respective wave mode and the reflected ray characteristic of the test head.

Since, as is known, the echo amplitude is not proportional to the size of fault, in the evaluation method according to the invention, in the range exceeding the threshold the high frequency signal can be subjected to a signal analysis. Known methods of analysis according to phase and signal rise (cf. German patent application No. 28 40 748) can be carried out with the digitalized signal, and lead to an objective assessment of the fault. All fault signals are stored intermediately together with corresponding characteristic quantities and serve, if required, for the numerical activation of the fault reworking unit.

Image processing systems, for example, are particularly suitable for on-line processing of the digital signals arising, which systems, owing to their possible high data processing rates make a real time evaluation possible.

The evaluation concept is explained by way of example in the example of a four-channelled testing installation for the surface testing of large pipes (FIG. 1).

The test heads emit signals in cyclic sequence to the A-D transducers 1a to 1d associated with the four channels which in turn pass the resulting HF-signals on to the averaging units 2a to 2d. In the multiplexer 3, HF-signals averaged according to the cycle scheme, are transferred to a digital rectifier unit 4 and subsequently are filtered digitally in 5, corresponding to the filter characteristics of the individual channels stored in 6a to 6d. In the threshold evaluation unit 6 an evaluation of this signal takes place with specifiable threshold characteristics 7a to 7d. On exceeding the threshold, with the aid of the space coordinate counter 8 the position of the fault is calculated and the positions are intermediately stored on the memory 9. In addition, on exceeding the threshold, a signal analysis of the averaged HF-signal takes place in the HF-signal analysis unit 10, in order to obtain data regarding the sizes of fault.

In completion of the on-line testing process, the intermediately stored data are transferred for documention onto a quantity memory 11, a video screen 12 and to a fault treatment unit 13 connected at the outlet side. The entire sequence control is undertaken here by the process control computer 14.

It is further contemplated as a portion of the invention that several ultrasonic waves may be produced at different positions on the test piece, the HF-signals of which are processed successively. Further, it is contemplated that several wave modes may be produced, received and assessed independently of each other in successive cycles of operation.

We claim:

1. A method for non-destructive testing of a test piece for faults, using guided waves in cyclic production and reception of ultrasonic waves, through the assessment of the received HF-signals for signal components which derive from faults and through the evaluation of the result, comprising the steps of:

digitizing said received HF-signals;
generating average values of successive digitized HF-signals;
rectifying said average values;
filtering said average values;
assessing said average values with an assessment unit against a threshold value and analyzing average values for faults within a testing path;
wherein several ultrasonic waves are produced at different positions on the test piece, the HF-signals of which are multiplexed and processed successively by said assessment unit; and
wherein several wave modes are introduced to the test piece and assessed independently of each other.

* * * * *